(12) United States Patent
Tsao et al.

(10) Patent No.: US 12,364,560 B2
(45) Date of Patent: Jul. 22, 2025

(54) RAPID AND PRECISE TOOL EXCHANGE MECHANISM FOR INTRAOCULAR ROBOTIC SURGICAL SYSTEMS

(71) Applicant: THE REGENTS OF THE UNIVERSITY OF CALIFORNIA, Oakland, CA (US)

(72) Inventors: Tsu-Chin Tsao, Manhattan Beach, CA (US); Matthew Gerber, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1047 days.

(21) Appl. No.: 16/982,506

(22) PCT Filed: Mar. 20, 2019

(86) PCT No.: PCT/US2019/023193
§ 371 (c)(1),
(2) Date: Sep. 18, 2020

(87) PCT Pub. No.: WO2019/183236
PCT Pub. Date: Sep. 26, 2019

(65) Prior Publication Data
US 2021/0015573 A1 Jan. 21, 2021

Related U.S. Application Data

(60) Provisional application No. 62/646,158, filed on Mar. 21, 2018.

(51) Int. Cl.
*A61B 34/35* (2016.01)
*A61B 34/00* (2016.01)
(Continued)

(52) U.S. Cl.
CPC .............. *A61B 34/72* (2016.02); *A61B 34/35* (2016.02); *A61B 34/37* (2016.02); *B25J 5/007* (2013.01)

(58) Field of Classification Search
CPC ......... A61B 34/72; A61B 34/35; A61B 34/37; B25J 5/007
See application file for complete search history.

(56) References Cited

U.S. PATENT DOCUMENTS

| 5,340,248 A | 8/1994 | Enbergs |
| 6,478,681 B1 * | 11/2002 | Overaker ........... A61B 17/1624 464/29 |

(Continued)

FOREIGN PATENT DOCUMENTS

CN 107280768 A 10/2017

OTHER PUBLICATIONS

Foreign Action other than Search Report on EP 19771125.2 DTD Nov. 22, 2021.
(Continued)

*Primary Examiner* — Katherine M Rodjom
(74) *Attorney, Agent, or Firm* — Foley & Lardner LLP

(57) ABSTRACT

A system for intraocular robotic surgery includes: (1) a set of mounts to receive a tool collar to which a surgical tool is secured; (2) a rotational actuator connected to the set of mounts to drive rotation of the set of mounts; and (3) a translational actuator connected to the set of mounts to drive linear translation of the set of mounts.

18 Claims, 7 Drawing Sheets

(51) Int. Cl.
*A61B 34/37* (2016.01)
*B25J 5/00* (2006.01)

(56) References Cited

U.S. PATENT DOCUMENTS

| | | | |
|---|---|---|---|
| 9,687,607 B2 | 6/2017 | Brereton et al. | |
| 2008/0119872 A1 | 5/2008 | Brock et al. | |
| 2011/0130718 A1* | 6/2011 | Kidd | A61B 34/30 |
| | | | 604/95.01 |
| 2013/0211397 A1 | 8/2013 | Parihar et al. | |
| 2014/0066944 A1 | 3/2014 | Taylor et al. | |
| 2015/0173838 A1* | 6/2015 | Murphy | A61B 34/30 |
| | | | 606/130 |
| 2016/0157941 A1* | 6/2016 | Anvari | A61B 34/70 |
| | | | 279/143 |
| 2016/0228205 A1 | 8/2016 | Nambi et al. | |
| 2016/0361126 A1 | 12/2016 | Schena et al. | |
| 2016/0374769 A1 | 12/2016 | Schena et al. | |
| 2017/0252208 A1 | 9/2017 | Meenink | |
| 2021/0177528 A1* | 6/2021 | Cappelleri | A61B 34/30 |

OTHER PUBLICATIONS

Foreign Action other than Search Report on EP 19771125.2 DTD Dec. 9, 2021.
Foreign Action other than Search Report on PCT PCT/US2019/023193 Dtd Oct. 1, 2020.
International Search Report on PCT/US2019/023193 Dtd Jun. 19, 2019.
Wilson et al., "Intraocular Robotic Interventional Surgical System (IRISS): Mechanical Design, Evaluation and Master-Slave Manipulation," Apr. 23, 2017, Retrieved from Internet on May 19, 2019, URL: https://www.ncbi.nlm.nih.gov/pubmed/28762253.
Examination Report on European Application No. 19771125.2 date Feb. 19, 2025 (4 pages).

* cited by examiner

RAPID AND PRECISE TOOL EXCHANGE MECHANISM FOR INTRAOCULAR ROBOTIC SURGICAL SYSTEMS

CROSS-REFERENCE TO RELATED APPLICATIONS

This application is a National Stage Entry of International Application No. PCT/US2019/023193, filed Mar. 20, 2019, which claims the benefit of and priority to U.S. Provisional Application No. 62/646,158, filed Mar. 21, 2018, the contents of which are incorporated herein by reference in their entirety.

STATEMENT REGARDING FEDERALLY SPONSORED RESEARCH OR DEVELOPMENT

This invention was made with government support under Grant Number EY024065, awarded by the National Institutes of Health. The Government has certain rights in the invention.

TECHNICAL FIELD

This disclosure relates generally to a tool exchange mechanism for surgical instruments or tools in intraocular robotic surgical systems. In particular, this disclosure relates to facilitating tool exchange in a precise, repeatable, and rapid manner.

BACKGROUND

Intraocular medical conditions are treated with delicate microsurgical procedures such as cataract surgery, pars plana vitrectomy, and epiretinal membrane dissection. Undesired surgical complications can be significantly decreased through the use of robotic surgical systems such as teleoperated systems that attenuate undesirable movement and can position a surgical instrument or tool with high degrees of accuracy and precision. Such robotic surgical systems can provide various benefits over traditional surgical techniques including shorter operation times, reduced recovery times, and decreased cost.

However, intraocular surgical procedures are multistep processes that involve the use of several tools such as a retinal pic, a vitreous cutter, and an infusion-aspiration probe, among others of various sizes and shapes. In addition, for a given surgical procedure, there are typically (at most) three entry sites through a sclera, and surgical instruments or tools for the surgical procedure are constrained to pass through these sites. Therefore, due both to the multistep nature of intraocular microsurgical procedures, as well as a constrained number of entry sites in such procedures, it is desired to provide a mechanism to exchange one surgical instrument for another instrument to perform different functions. Furthermore, a mechanism to exchange tools rapidly is desirable for reasons of timing and safety.

It is against this background that a need arose to develop the embodiments described herein.

SUMMARY

Embodiments of this disclosure are directed to a mechanism for rapid, precise, and repeatable removal and replacement of surgical instruments or tools during surgical procedures, such as intraocular surgical procedures. The tool exchange mechanism can be equipped on-board a robotic surgical system. The tool exchange mechanism can accommodate arbitrary tool sizes and shapes and can allow for accurate and precise actuation of translational motion and rotational motion of a mounted tool.

In some embodiments, a tool exchange mechanism includes (1) a set of mounts for receiving a tool collar to which a surgical instrument or tool is secured; (2) a coupling mechanism for securing the tool collar, along with the surgical instrument or tool, to the mounts while allowing for low-force removal of the tool collar, along with the surgical instrument or tool, from the mounts; (3) a rotational actuator to drive rotation of the tool collar, along with the surgical instrument or tool, about its centerline; and (4) a translational actuator to drive linear translation of the tool collar, along with the surgical instrument or tool, along its centerline. In some embodiments, the tool exchange mechanism in combination with a set of tool collars provide a tool exchange system, where each tool collar is configured to receive and secure a surgical instrument or tool of arbitrary size, shape, or dimension, and is configured to provide a common or universal interface received by the tool mounts.

In some embodiments, a system of mounts and tool collars can facilitate precise and repeatable tool exchange. The system of mounts and tool collars can kinematically constrain a surgical instrument or tool received in a set of mounts in a single, repeatable manner. The mounts can allow for self-alignment of the surgical instrument or tool received in the mounts. A force-based coupling mechanism can be included to secure the surgical instrument or tool to the mounts. Furthermore, ample physical space can be provided to accommodate surgical tubing and wiring and can also provide stress relief for tubing, fiber optic cable, and electrical wiring, thereby reducing or eliminating physical interference between cables and other moving components.

Embodiments can be applied to an intraocular robotic system for minimally invasive surgery or other applications that specify precise (and repeatable) and rapid tool exchange or replacement. A comparative approach for tool exchange can involve custom-designed tool collars and mounts which are then rigidly secured to a tool carriage or transporter. This comparative approach involves accurate and time-consuming calibration and positioning off-line, which may have to be performed every time a surgery occurs. In contrast, embodiments of a tool exchange mechanism allow for rapid, low-force removal of a surgical instrument or tool and rapid, low-force replacement of another surgical instrument or tool into a set of controllable mounts. Geometric constraints of the mounts and a tool collar are such that a surgical instrument or tool can be readily and repeatedly mounted with high precision and accuracy, while omitting post-mounting calibration or tuning.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Embodiments of this disclosure relate to a tool exchange mechanism in a robotic surgical system, such as one used to perform intraocular surgical procedures. In some embodiments, the tool exchange mechanism is configured to secure a surgical instrument or tool to a set of constraining mounts while allowing for rotational motion and translational motion of the tool. The mechanism allows for rapid and precise tool exchange such that a relatively small force is applied to remove a surgical instrument or tool from the set of mounts, but a removed surgical instrument or tool can be repeatedly returned to a kinematically precise location and orientation via the set of mounts and a tool collar. The mechanism allows for fine-motion tuning of a tool position within its collar and can secure any arbitrary tool size or shape.

Figure 1:
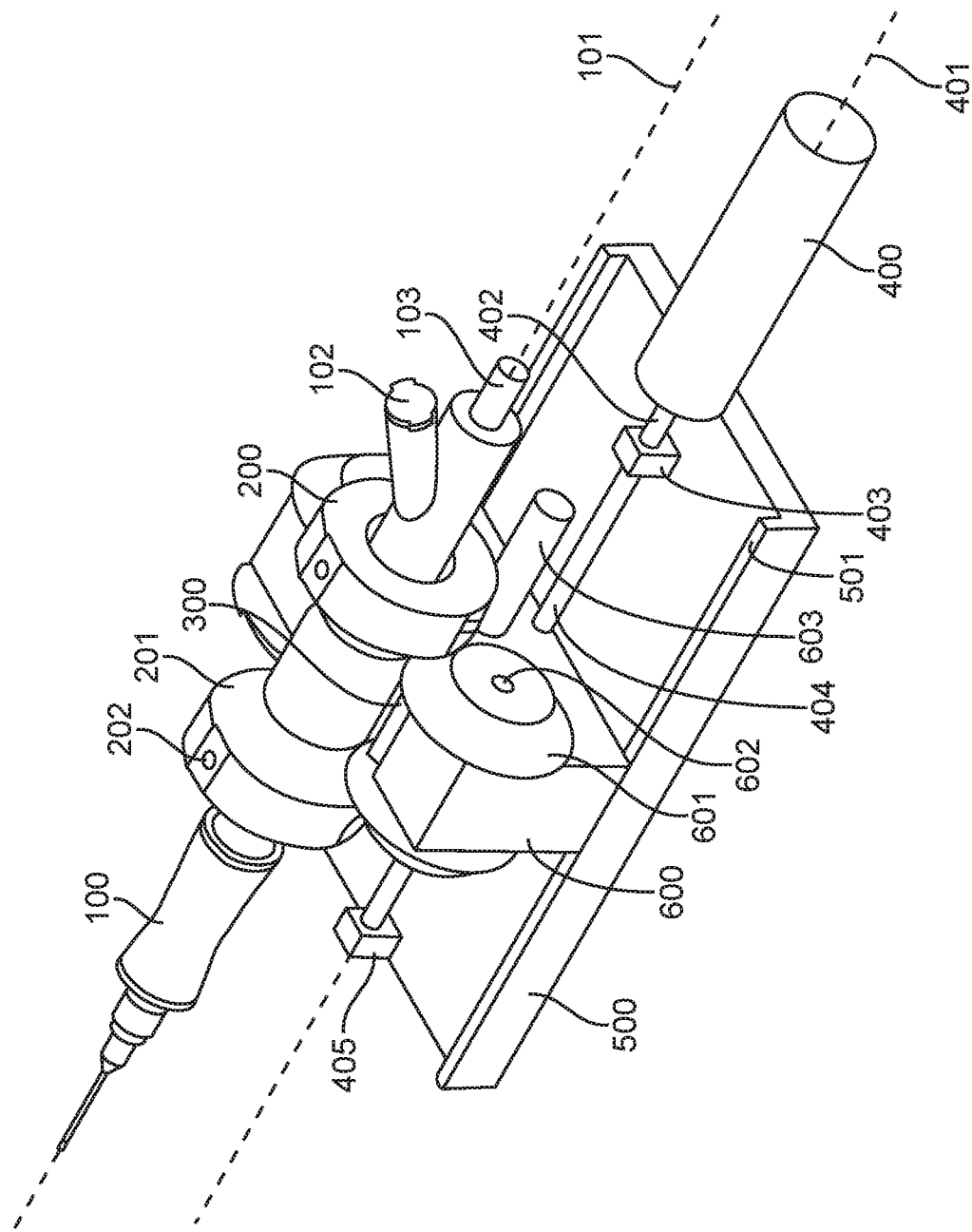
FIG. 1. A perspective view of some embodiments of a tool exchange mechanism to which a surgical tool is mounted.
Figure 2:
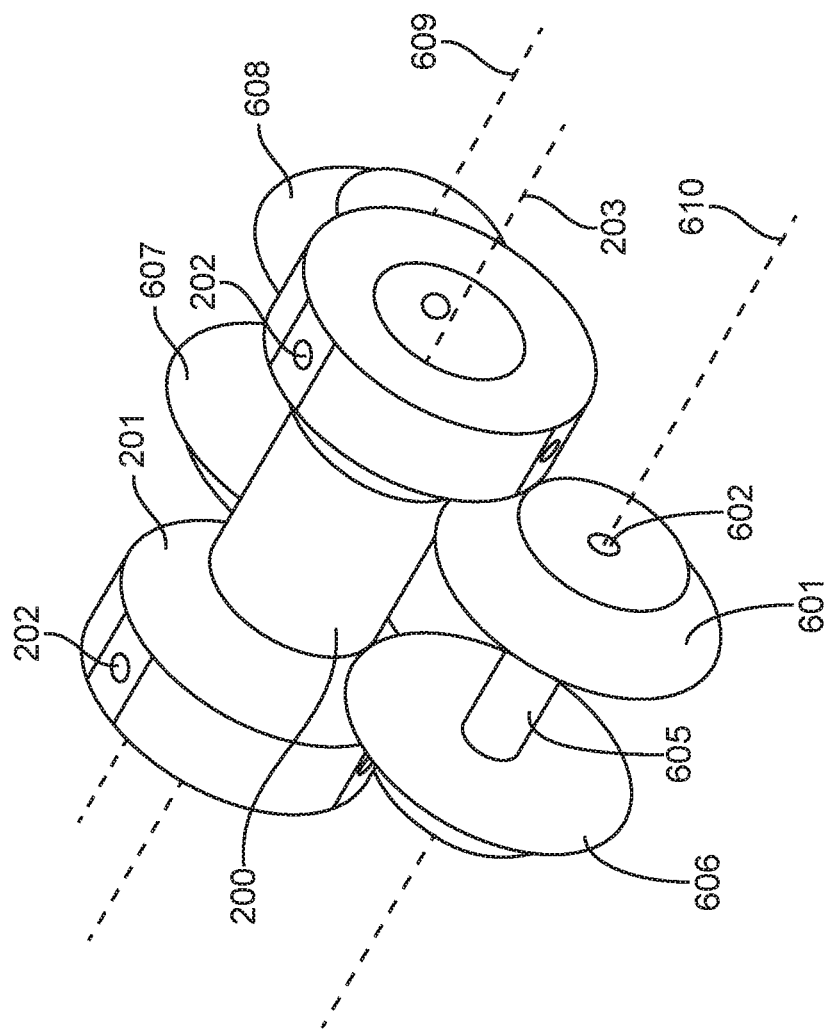
FIG. 2. A perspective view of some embodiments of a surgical tool collar mounted to a set of mounts included in a tool exchange mechanism.

To allow for tool exchange in a precise, repeatable, and rapid manner, a tool carriage 10 (see FIGS. 6 and 7) is configured to include a tool exchange mechanism. FIG. 1 is a perspective view of some embodiments of the tool exchange mechanism to which a surgical tool 100 is mounted, and FIG. 2 is a perspective view of some embodiments of a surgical tool collar 200 mounted to a set of mounts included in the tool exchange mechanism. The surgical tool 100 is mounted while allowing rotation about its centerline 101. The surgical tool 100 includes back ports 102 and 103, which can freely rotate about the tool centerline 101 without physical interference between the back ports 102 and 103 and other components. The mounted surgical tool 100 is secured to an inside of the tool collar 200 such that the tool centerline 101 is substantially aligned, coincident, or collinear with a centerline 203 of the tool collar 200. The surgical tool 100 is secured to the tool collar 200 via a clamping mechanism, such as a set of securing screws 202 as explained further below with reference to FIG. 4.

The tool collar 200 is mounted and secured to the set of tool mounts in the form of a first pair of mounting wheels 601 and 606 and a second pair of mounting wheels 607 and 608, such that their interface with the tool collar 200 can ensure a constraint space similar to that of a kinematic coupling. That is to say, the mounted surgical tool 100 secured inside the tool collar 200 is received and fits into the mounting wheels 601, 606, 607, and 608 in a single, repeatable manner that is self-aligning and allows omission of post-mounting adjustment. Each pair of mounting wheels 601 and 606 (or 607 and 608) is mounted to a respective rotational shaft 602. Rotation of the first pair of mounting wheels 601 and 606 and the second pair of mounting wheels 607 and 608 about their rotational shafts 602 results in rotation of the mounts-to-collar interface. Rotation of the first pair of mounting wheels 601 and 606 and the second pair of mounting wheels 607 and 608 about their respective centerlines 610 and 609 results in rotation of the tool collar 200 and thereby results in rotation of the mounted surgical tool 100. The first pair of mounting wheels 601 and 606 and the second pair of mounting wheels 607 and 608 are mounted to a base 500 via a sliding carriage 600 housing the rotational shafts 602, and the rotational shafts 602 are movably mounted to the sliding carriage 600 such that the mounting wheels 601, 606, 607, and 608 can freely rotate with respect to the sliding carriage 600.

Figure 3A:
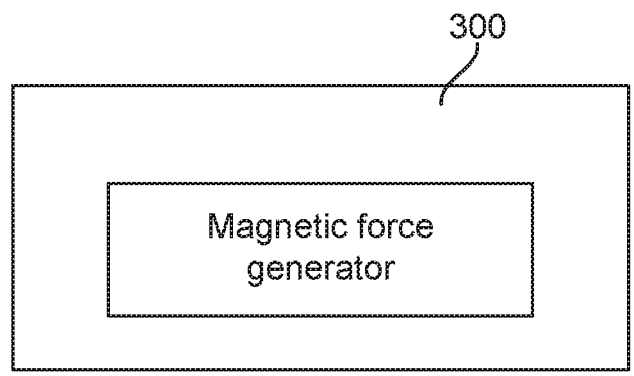
FIG. 3. Schematics of some embodiments of a coupling mechanism to securely fasten a tool collar to a set of mounts.
Figure 3B:
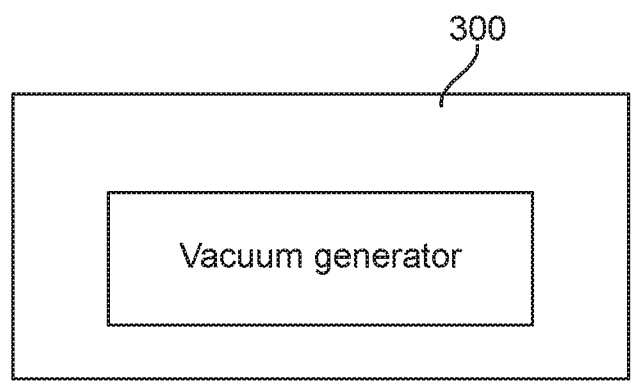
Figure 3C:
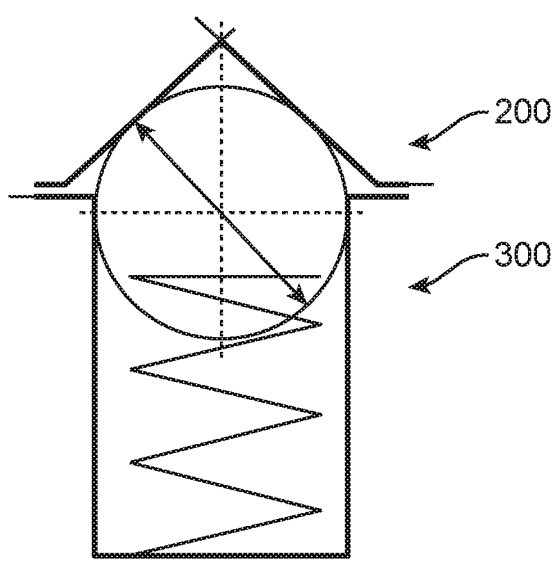

Housed in, or mounted to, the sliding carriage 600 is a force-based coupling mechanism 300 that securely fastens the tool collar 200 to the mounting wheels 601, 606, 607, and 608 and to the sliding carriage 600. The mounted surgical tool 100 and the tool collar 200 can be secured to the mounting wheels 601, 606, 607, and 608 through a variety of techniques, such as a controllable electromagnetic force; a mechanically adjustable or non-adjustable static magnetic force; a vacuum force; a detenting mechanism; or a combination of two or more thereof. In some embodiments of a magnetic force for the coupling mechanism 300, the tool collar 200 can include a ferromagnetic material, and the coupling mechanism 300 can include a generator of a magnetic force (see FIG. 3(*a*)). In some embodiments of a vacuum force for the coupling mechanism 300, the tool collar 200 can include a sealable surface, a mechanism, or a material capable of forming an air-tight seal with a vacuum generator included in, or connected to, the coupling mechanism 300 (see FIG. 3(*b*)). A vacuum force can be continuously applied or applied once and statically maintained. In some embodiments of a detenting mechanism, a ball or a pin actuated by a mechanical spring, compressed air, electromagnetic force, or other force included in or imparted by the coupling mechanism 300 can engage a socket, groove, or another mechanism in the tool collar 200 and can secure the tool collar 200 in place (see FIG. 3(*c*)).

The coupling mechanism 300 applies a restraining force to secure the tool collar 200 in place until a sufficiently large force is exerted to disengage the tool collar 200. For example, such a force can be applied in the event of a planned tool exchange, a routine maintenance, or a fail-safe disengagement. In some embodiments, the mounted surgical tool 100 can be firmly secured in the tool collar 200 by the mounting wheels 601, 606, 607, and 608 to allow surgical manipulation of the mounted surgical tool 100 without unintended disengagement while ensuring a release force is not prohibitively large for purposes of fast, safe, and non-disruptive removal of the mounted surgical tool 100. A restraining force can also be sufficiently strong to resist failure and can substantially eliminate toggle, play, or independent movement of the mounted surgical tool 100.

The mounting wheels 601, 606, 607, and 608 are driven to rotate by a rotational actuator 603 housed in, or mounted to, the sliding carriage 600, such that rotation of the mounting wheels 601, 606, 607, and 608 in turn results in rotation of the mounted surgical tool 100. A power transmission mechanism can be housed in, or mounted to, the sliding carriage 600, such that the actuator 603 drives the rotation of the mounted surgical tool 100 via the power transmission mechanism.

Figure 6:
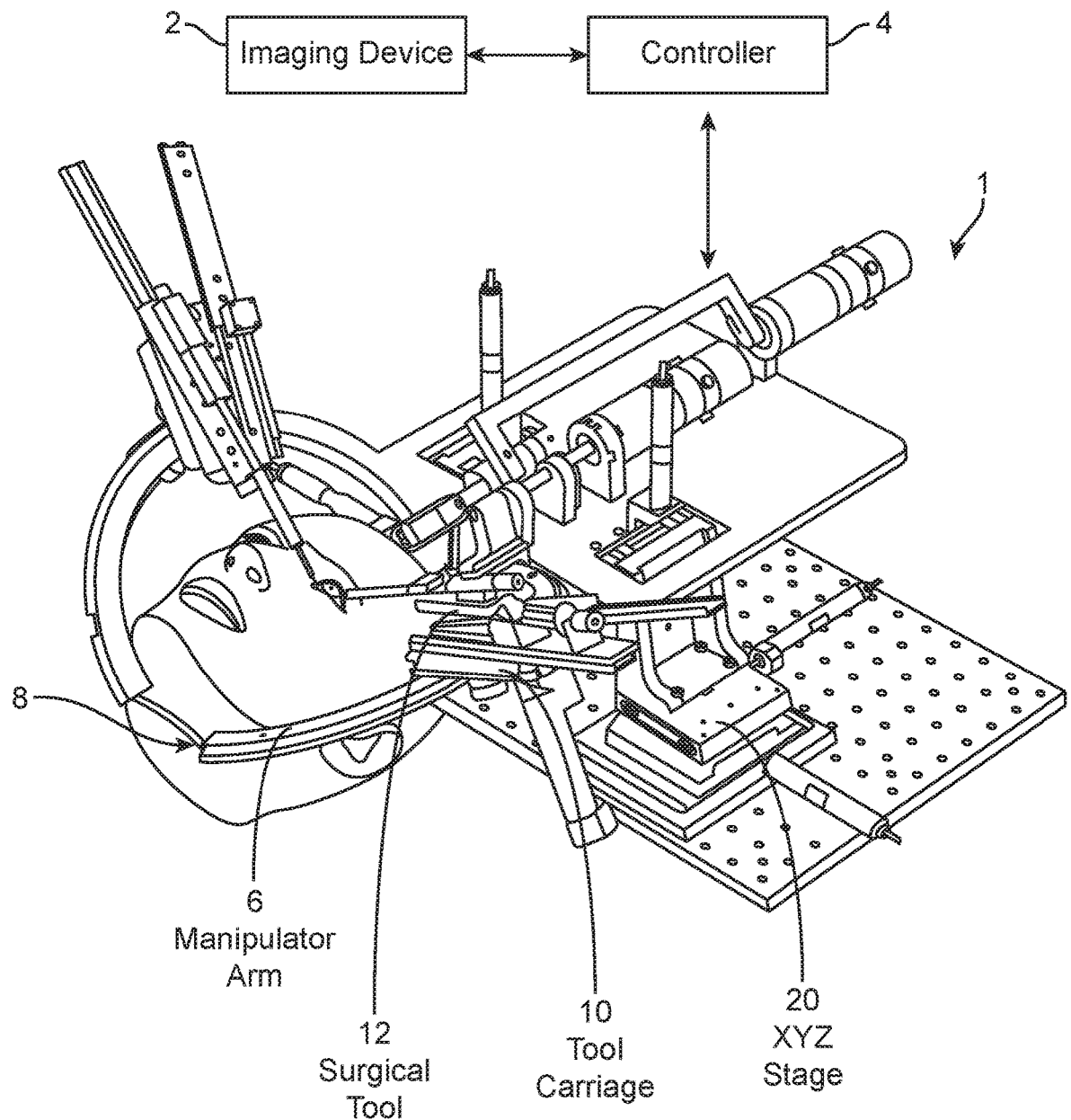
FIG. 6. A robotic surgical system according to some embodiments.
Figure 7:
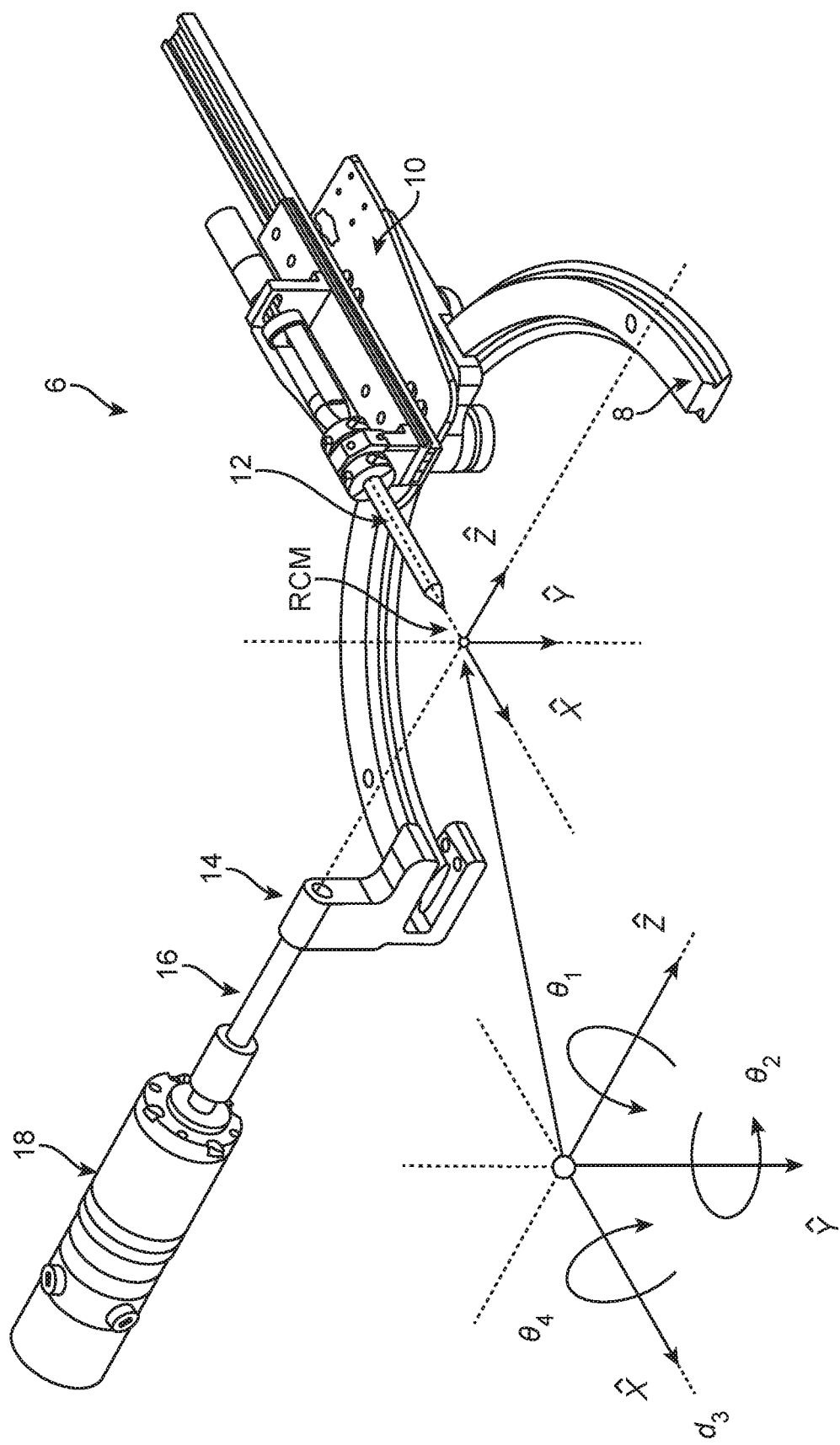
FIG. 7. A manipulator arm included in a robotic surgical system according to some embodiments.

The base 500 can be mounted to a manipulator arm 6 as shown in FIGS. 6 and 7, or another operating platform for purposes of conducting surgery. The sliding carriage 600 is movably mounted to the base plate 500 to allow translational motion in a direction along an axis 401. As shown in FIG.

1, the base 500 includes a linear slider 501 to allow translational motion of the sliding carriage 600, although another mechanism can be included. Translational motion of the sliding carriage 600 along the linear slider 501 is driven by rotation of a translational actuator 400 about the axis 401, thereby moving the mounted surgical tool along 100 via translational motion. The actuator 400 is connected to a rear bearing block 403 via an actuator coupling 402, and the rear bearing block 403 is connected to the sliding carriage 600 via a power transmission shaft 404, which can be implemented through a capstan/friction drive bar, a lead screw, or another mechanism. The power transmission shaft 404 is connected to the sliding carriage 600 such that rotation of the actuator 400 about the axis 401 results in translation of the sliding carriage 600. A forward bearing block 405 can also be included to support the power transmission shaft 404.

With reference to FIG. 2, the tool collar 200 has the tool collar centerline 203 about which it may rotate. A surgical tool can be secured to the tool collar 200 via a clamping mechanism included in the tool collar 200. Surfaces 201 of the tool collar 200 can interface with surfaces of the mounting wheels 601, 606, 607, 608 such that a kinematic alignment is obtained. The mounting wheels 601, 606, 607, 608 together can connect to the tool collar 200. Rotation of the mounting wheels 601, 606, 607, 608 about the centerlines 610 and 609 results in rotation of the tool collar 200 about the tool collar centerline 203.

Figure 4:
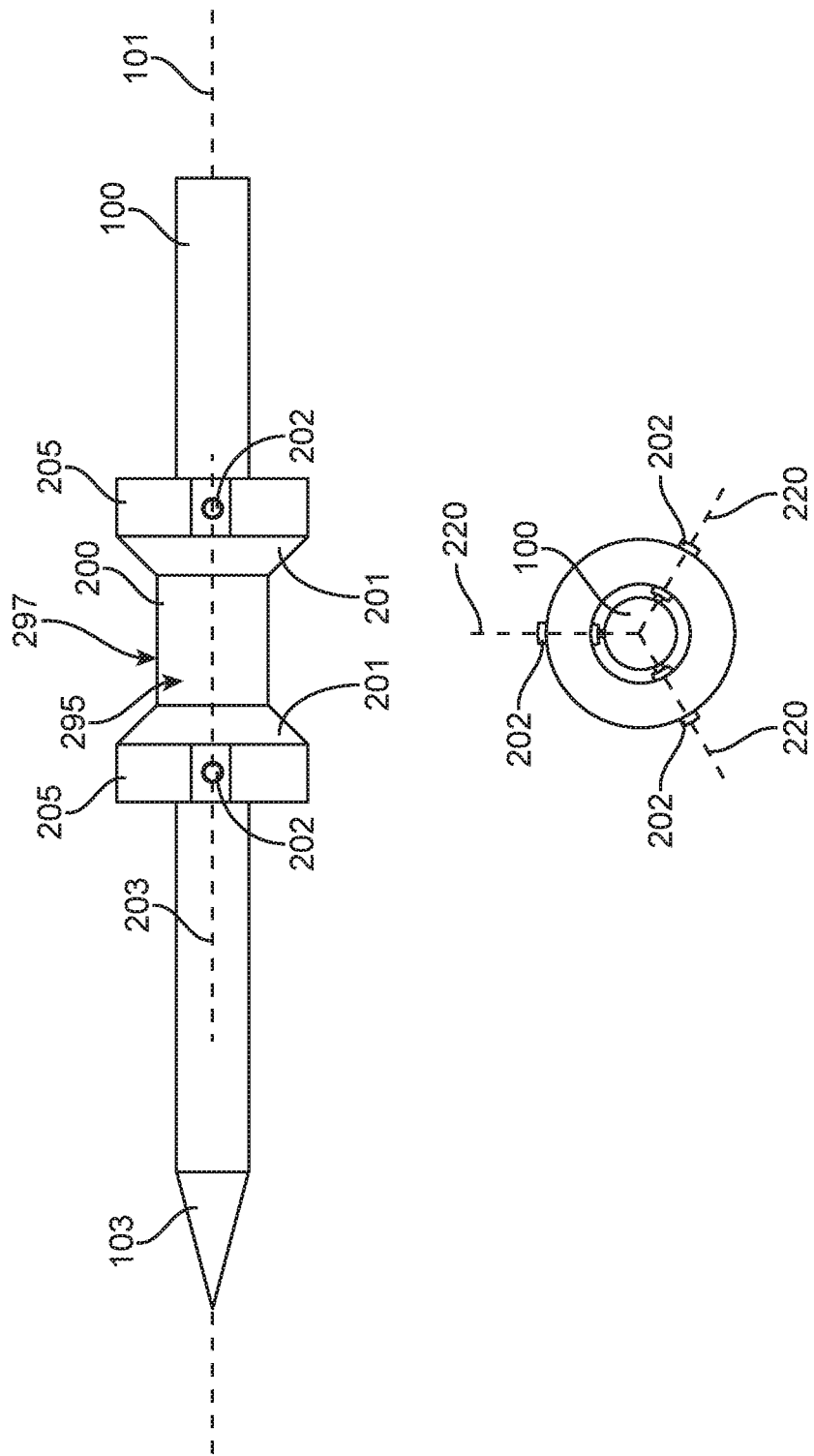
FIG. 4. A schematic of some embodiments of a surgical tool collar to which a surgical tool is secured via a clamping mechanism.

With reference to FIG. 4, a schematic of some embodiments of the tool collar 200 is shown, along with an example of the surgical tool 100 that is secured to the tool collar 200. The tool collar 200 includes a hollow tool collar body 295 and a pair of support rings 205 at respective ends of the tool collar body 295 and including the tool collar mounting surfaces 201. As shown in FIG. 4, the tool collar mounting surfaces 201 are beveled or slanted with respect to an exterior surface 297 of the tool collar body 295, each forming an angle different from 90 degrees with respect to the exterior surface 297, and, in particular, greater than 90 degrees and less than 180 degrees, such as about 100 degrees or greater, about 110 degrees or greater, about 120 degrees or greater, or about 130 degrees or greater. Each of the support rings 205 includes a clamping mechanism in the form of a set of securing screws 202, which can be rotated to move along respective axes 220 to engage or disengage from the surgical tool 100. The tool collar centerline 203 can be substantially aligned, coincident, or collinear with a geometric centerline of the tool collar 200. The surgical tool 100 includes a tool body and a tool tip 103 at one end of the tool body, and the surgical tool 100 has the surgical tool centerline 101 about which it can rotate or translate.

It is desirable that the surgical tool centerline 101 is maintained as substantially aligned, coincident, or collinear with the tool collar centerline 203. Achieving this collinearity can involve adjusting the screws 202 along their respective axes 220. In some embodiments, a minimum of four mounting screws 202 can be included to adjust four degrees of freedom of the surgical tool 100.

Figure 5:
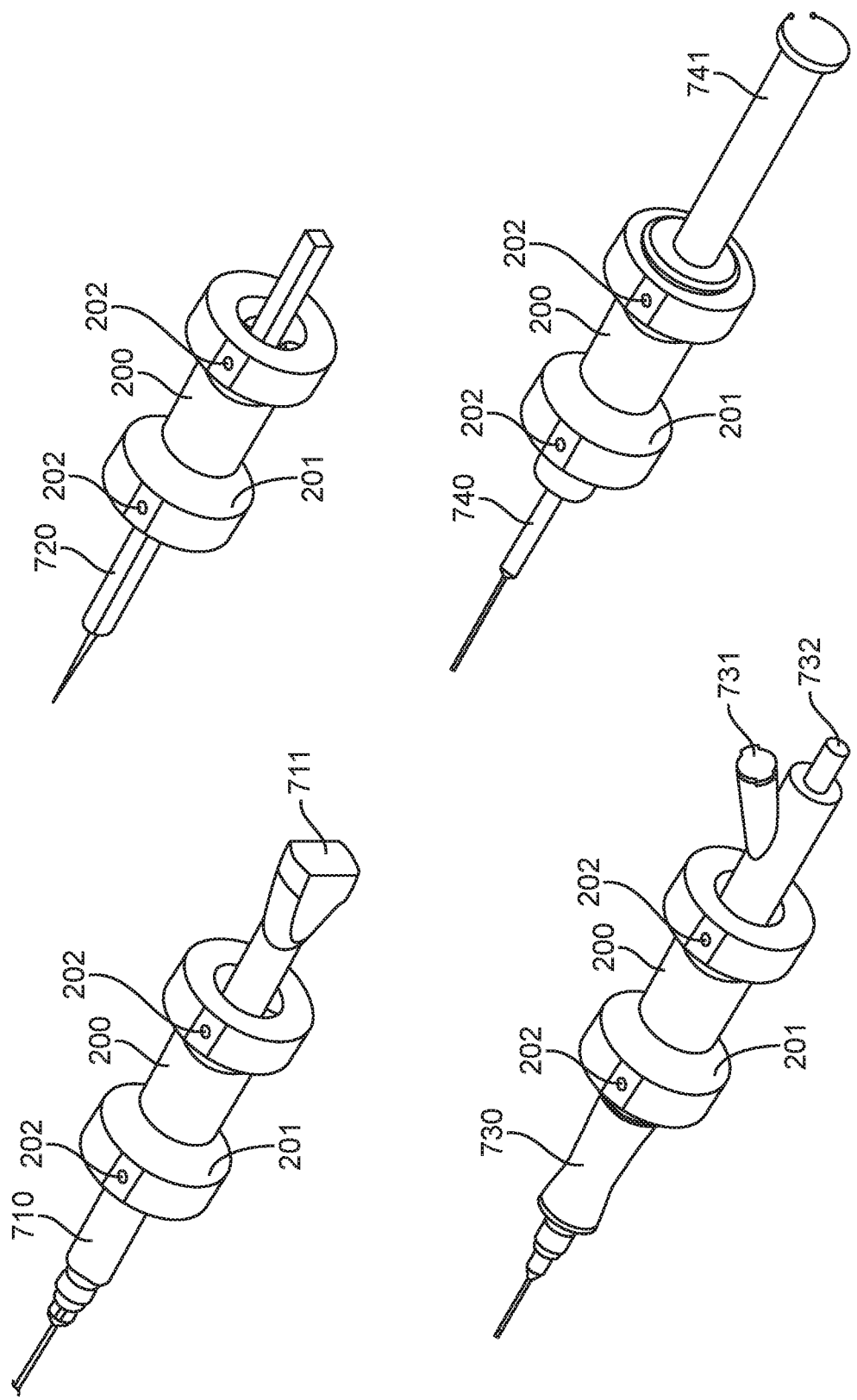
FIG. 5. A schematic of some embodiments of a surgical tool collar interfacing with various examples of surgical tools.

With reference to FIG. 5, schematic diagrams are provided for some embodiments of the tool collar 200 that can be used to secure various different tools through the screws 202. An example tool 710 is an irrigation/aspiration probe with a rear port 711 that can incorporate a set of tubes. An example tool 720 is a retinal pic, which has a non-circular or non-uniform cross-sectional shape. An example tool 730 is another irrigation/aspiration probe with rear ports 731 and 732 that can incorporate a set of tubes. An example tool 740 is a visco-elastic syringe including a rear plunger 741, for which additional space is provided to accommodate actuation of the plunger 741.

FIG. 6 shows a robotic surgical system according to some embodiments. The system includes a surgical manipulator 1, an imaging device 2, and a controller 4. The imaging device 2 can include a surgical microscope (e.g., a stereoscopic ophthalmic microscope), a camera, or both. The controller 4 is connected to the surgical manipulator 1 and the imaging device 2, and directs operation of the surgical manipulator 1 and the imaging device 2. The controller 4 can be implemented as a processor and an associated memory.

As shown in FIG. 6, the surgical manipulator 1 includes a pair of independently controllable manipulator arms 6, each including a semi-circular track 8 to which the tool carriage 10 is moveably mounted, and where the tool carriage 10 holds one or more surgical instruments or tools 12 that are moveably mounted to the tool carriage 10. Each surgical tool 12 is mechanically constrained about a remote center of motion (RCM) of the manipulator arm 6 to which the surgical tool 12 is mounted, such that that an axis or centerline of the surgical tool 12 extends through the RCM while remaining in a planar region specified based on a rotational orientation of the manipulator arm 6. Robotic motion of various components of the manipulator arms 6 is driven by actuators, such as motors and associated drive electronics, as directed by the controller 4. Although the two manipulator arms 6 are shown in the FIG. 6, more than two or a single one of such manipulator arms 6 can be included in other embodiments.

A single one of the manipulator arms 6 is shown in FIG. 7, according to some embodiments. Additional manipulator arms 6 can be similarly configured as explained below. The RCM of the manipulator arm 6 is mechanically enforced by mounting the surgical tool 12 to the tool carriage 10 that is slidable along the semi-circular track 8, allowing rotation about $Ŷ$ by $\theta_2$. The semi-circular track 8 is mounted to a rotational joint 14, which allows rotation about $Ẑ$ by $\theta_1$. The semi-circular track 8 and the rotational joint 14 are aligned such that their rotational axes are substantially orthogonal and intersect at the RCM. The surgical tool 12 is mounted such that its axis or centerline intersects the axis of rotation of the semi-circular track 8 and passes through the RCM. In this manner, in-and-out translational motion of the tool 12 is denoted as $d_3$, and rotation of the tool 12 about its centerline is denoted as $\theta_4$. The semi-circular track 8 is mounted, via the rotational joint 14, to a rotational shaft 16 that is driven to rotate by an actuator 18, such as a motor and associated drive electronics. An axis of rotation of the shaft 16 is substantially coincident with the axis of rotation of the rotational joint 14.

Referring back to FIG. 6, to allow three-dimensional translation of the mechanically constrained RCMs, the manipulator arms 6 are mounted to a multi-axis positioning stage 20 capable of three-dimensional XYZ translation. Translational motion of the stage 20 is driven by a set of actuators, such as motors and associated drive electronics.

Example Embodiments

The following are example embodiments of this disclosure.
First Aspect

In some embodiments, a system for intraocular robotic surgery includes: (1) a set of mounts to receive a tool collar to which a surgical tool is secured; (2) a rotational actuator connected to the set of mounts to drive rotation of the set of mounts; and (3) a translational actuator connected to the set of mounts to drive linear translation of the set of mounts.

In some embodiments, the set of mounts includes a set of mounting wheels. In some embodiments, the set of mounting wheels includes a first pair of mounting wheels and a second pair of mounting wheels spaced from the first pair of mounting wheels to receive the tool collar in between. In some embodiments, the system further includes a base and a sliding carriage movably mounted to the base, and the set of mounting wheels are mounted to the base via the sliding carriage.

In some embodiments, the system further includes a coupling mechanism to secure the tool collar to the set of mounts. In some embodiments, the coupling mechanism is configured to apply an electromagnetic force, a magnetic force, or a vacuum force. In some embodiments, the coupling mechanism includes a detenting mechanism.

In some embodiments, the system further includes the tool collar, wherein the tool collar includes a clamping mechanism to secure the surgical tool.

In some embodiments, the system further includes a positioning stage and a manipulator arm mounted to the positioning stage, wherein the manipulator arm includes a tool carriage including the set of mounts, the rotational actuator, and the translational actuator.

Second Aspect

In additional embodiments, a system for intraocular robotic surgery includes: (1) a base; (2) a sliding carriage movably mounted to the base; (3) a set of mounting wheels movably mounted to the sliding carriage; (4) a rotational actuator mounted to the sliding carriage and connected to the set of mounting wheels to drive rotation of the set of mounting wheels; and (5) a translational actuator connected to the sliding carriage to drive linear translation of the sliding carriage.

In some embodiments, the set of mounting wheels includes a first pair of mounting wheels and a second pair of mounting wheels spaced from the first pair of mounting wheels. In some embodiments, the first pair of mounting wheels is spaced from the second pair of mounting wheels to receive a tool collar between the first pair of mounting wheels and the second pair of mounting wheels. In some embodiments, the sliding carriage includes a first rotational shaft and a second rotational shaft, and the first pair of mounting wheels and the second pair of mounting wheels are movably mounted to the sliding carriage via the first rotational shaft and the second rotational shaft, respectively.

In some embodiments, the system further includes a power transmission shaft, and the translational actuator is connected to the sliding carriage via the power transmission shaft.

In some embodiments, the system further includes a positioning stage and a manipulator arm mounted to the positioning stage, wherein the manipulator arm includes a tool carriage including the base, the sliding carriage, the set of mounting wheels, the rotational actuator, and the translational actuator.

Third Aspect

In further embodiments, a tool collar includes: (1) a hollow body; and (2) a pair of support rings at respective ends of the hollow body, wherein each of the support rings includes a clamping mechanism to secure a surgical tool extending within the hollow body and the support rings.

In some embodiments, the clamping mechanism includes a set of securing screws.

In some embodiments, the hollow body includes an exterior surface, and each of the support rings includes a tool collar mounting surface which is slanted with respect to the exterior surface of the hollow body.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "connect," "connected," and "connection" refer to an operational coupling or linking. Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

In the description of some embodiments, an object provided "on," "over," "on top of," or "below" another object can encompass cases where the former object is directly adjoining (e.g., in physical or direct contact with) the latter object, as well as cases where one or more intervening objects are located between the former object and the latter object.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A system for intraocular robotic surgery, comprising:
   a tool collar having a clamping mechanism for removably securing a surgical tool;
   a set of mounts to receive the tool collar, wherein the tool collar is removably coupled to the set of mounts with one of an electromagnetic force, a magnetic force or a vacuum force;
   a rotational actuator connected to the set of mounts to drive rotation of the set of mounts, wherein the tool collar is configured to rotate by rotation of the set of mounts when the tool collar is coupled to the set of mounts; and
   a translational actuator connected to the set of mounts to drive linear translation of the set of mounts.

2. The system of claim 1, wherein the set of mounts includes a set of mounting wheels.

3. The system of claim 2, wherein the set of mounting wheels includes a first pair of mounting wheels and a second pair of mounting wheels spaced from the first pair of mounting wheels to receive the tool collar in between.

4. The system of claim 2, further comprising a base and a sliding carriage movably mounted to the base, wherein the set of mounting wheels are mounted to the base via the sliding carriage.

5. The system of claim 1, further comprising a coupling mechanism to secure the tool collar to the set of mounts.

6. The system of claim 5, wherein the coupling mechanism is configured to apply the one of an electromagnetic force, a magnetic force, or a vacuum force.

7. The system of claim 5, wherein the coupling mechanism includes a detenting mechanism.

8. The system of claim 1, further comprising a positioning stage and a manipulator arm mounted to the positioning stage, wherein the manipulator arm includes a tool carriage including the set of mounts, the rotational actuator, and the translational actuator.

9. A system for intraocular robotic surgery, comprising:
   a base;
   a sliding carriage movably mounted to the base;
   a tool collar having a clamping mechanism to removably secure a surgical tool;
   a set of mounting wheels movably mounted to the sliding carriage, wherein the tool collar is removably coupled to the set of mounting wheels with one of an electromagnetic force, a magnetic force or a vacuum force;
   a rotational actuator mounted to the sliding carriage and connected to the set of mounting wheels to drive rotation of the set of mounting wheels, wherein the tool collar is configured to rotate by rotation of the set of mounts when the tool collar is coupled to the set of mounts; and
   a translational actuator connected to the sliding carriage to drive linear translation of the sliding carriage.

10. The system of claim 9, wherein the set of mounting wheels includes a first pair of mounting wheels and a second pair of mounting wheels spaced from the first pair of mounting wheels.

11. The system of claim 10, wherein the first pair of mounting wheels is spaced from the second pair of mounting wheels to receive the tool collar between the first pair of mounting wheels and the second pair of mounting wheels.

12. The system of claim 10, wherein the sliding carriage includes a first rotational shaft and a second rotational shaft, and the first pair of mounting wheels and the second pair of mounting wheels are movably mounted to the sliding carriage via the first rotational shaft and the second rotational shaft, respectively.

13. The system of claim 9, further comprising a power transmission shaft, wherein the translational actuator is connected to the sliding carriage via the power transmission shaft.

14. The system of claim 9, further comprising a positioning stage and a manipulator arm mounted to the positioning stage, wherein the manipulator arm includes a tool carriage including the base, the sliding carriage, the set of mounting wheels, the rotational actuator, and the translational actuator.

15. A tool collar comprising:
    a hollow body; and
    a pair of support rings at respective ends of the hollow body,
    wherein each of the support rings includes a clamping mechanism to secure a surgical tool extending within the hollow body and the support rings, and
    wherein the support rings are configured to be removably coupled to a set of mounts with one of an electromagnetic force, a magnetic force or a vacuum force,
    and wherein the support rings are configured to allow for rotation of the surgical tool via rotation of the set of mounts when the support rings are coupled to the set of mounts.

16. The tool collar of claim 15, wherein the clamping mechanism includes a set of securing screws.

17. The tool collar of claim 16, wherein the tool collar has a tool collar centerline and the surgical tool has a surgical tool centerline, and wherein the securing screws are configured to cause the surgical tool centerline to be aligned with the tool collar centerline.

18. The tool collar of claim 15, wherein the hollow body includes an exterior surface, and each of the support rings includes a tool collar mounting surface which is slanted with respect to the exterior surface of the hollow body.

* * * * *